United States Patent
Chang et al.

(10) Patent No.: US 6,309,880 B1
(45) Date of Patent: Oct. 30, 2001

(54) ANTIBODIES SPECIFIC FOR CD4-BINDING DOMAIN OF HIV-1

(75) Inventors: Tse Wen Chang; Michael S. C. Fung, both of Houston; Bill N. C. Sun; Cecily R. Y. Sun, both of Bellaire; Nancy T. Chang, Houston, all of TX (US)

(73) Assignee: Tanox, Inc., Houston, TX (US)

( * ) Notice: Subject to any disclaimer, the term of this patent is extended or adjusted under 35 U.S.C. 154(b) by 0 days.

(21) Appl. No.: 08/089,990

(22) Filed: Jul. 9, 1993

Related U.S. Application Data

(63) Continuation-in-part of application No. 07/531,789, filed on Jun. 12, 1990, now abandoned, which is a continuation-in-part of application No. 07/342,950, filed on Apr. 25, 1989, now abandoned.

(51) Int. Cl.[7] .............................. C12N 5/06; C12N 5/16; C07K 16/00; C12P 21/08
(52) U.S. Cl. .................... 435/339.1; 435/328; 435/70.2; 435/452; 530/388.35; 530/387.3
(58) Field of Search ............................ 530/388.35, 387.3; 435/240.27, 172.2, 70.2, 328, 339.1, 452

(56) References Cited

FOREIGN PATENT DOCUMENTS

8601533 * 3/1986 (WO).
8707616 * 12/1987 (WO).

OTHER PUBLICATIONS

Morrison, Science 229: 1202–1207, 1985.*
Zolla–Pazner et al. J. Virological Mtds 17:45–53, 1987.*
Fahey et al., Clin. Exp. Immunol. 88:1–5 1992.*
Legrain et al., J. Virol. 60: 1141–44 (1986).
Robert–Guroff et al. 316 Nature 72–74 (1985).
Sun et al. J. Virology 63:3579–3585, 1989.*
Lasky et al. Cell 50: 975–985 1987.*
Brown et al. Molecular Immunology 24: 221–230, 1987.*

* cited by examiner

Primary Examiner—Yvonne Eyler
(74) Attorney, Agent, or Firm—Eric Mirabel

(57) ABSTRACT

A particular epitope located within the CD4-binding region of gp120 of HIV-1, and antibodies specific for the epitope which can inhibit HIV-1 infection of human cells by diverse strains and isolates of the virus, is disclosed. The antibodies are useful for a number of purposes, including diagnosis of HIV-1 infection.

4 Claims, No Drawings

SEQUENCE LISTING

```
(1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 15 amino acids (B) TYPE: amino acid (D) TOPOLOGY: linear (xi) SEQUENCE DESCRIPTION: SEQ ID NO:1:

Ile Ile Asn Met Trp Gln Lys Val Gly Lys Ala Met Tyr Ala Pro
1               5                   10                  15

(2) INFORMATION FOR SEQ ID NO:2:

(i) SEQUENCE CHARACTERISTICS:
          (A) LENGTH: 35 amino acids (B) TYPE: amino acid (D) TOPOLOGY: linear (xi) SEQUENCE DESCRIPTION: SEQ ID NO:2:

Thr Ile Thr Leu Pro Cys Arg Ile Lys Gln Ile Ile Asn Met Trp Gln Lys Val
1               5                   10                  15                  20

Lys Ala Met Tyr Ala Pro Pro Ile Ser Gly Gln Ile Arg Cys Ser Ser
20                  25                  30                  35

(2) INFORMATION FOR SEQ ID NO:3:

(i) SEQUENCE CHARACTERISTICS:
          (A) LENGTH: 15 amino acids (B) TYPE: amino acid (D) TOPOLOGY: linear
```

(xi) SEQUENCE DESCRIPTION: SEQ ID NO:3:

Thr Ile Thr Leu Pro Cys Arg Ile Lys Gln Ile Ile Asn Met Trp
1               5                   10                  15

(2) INFORMATION FOR SEQ ID NO:4:

(i) SEQUENCE CHARACTERISTICS:
        (A) LENGTH: 11 amino acids (B) TYPE: amino acid (D) TOPOLOGY: linear (xi) SEQUENCE DESCRIPTION: SEQ ID NO:4:

Gln Ile Ile Asn Met Trp Gln Lys Val Gly Lys
1               5                   10

(2) INFORMATION FOR SEQ ID NO:5:

(i) SEQUENCE CHARACTERISTICS:
        (A) LENGTH: 15 amino acids (B) TYPE: amino acid (D) TOPOLOGY: linear (xi) SEQUENCE DESCRIPTION: SEQ ID NO:5:

Ile Ile Asn Met Trp Gln Lys Gly Lys Val Ala Met Tyr Ala Pro
1               5                   10                  15

(2) INFORMATION FOR SEQ ID NO:6:

(i) SEQUENCE CHARACTERISTICS:
        (A) LENGTH: 15 amino acids (B) TYPE: amino acid (D) TOPOLOGY: linear (xi) SEQUENCE DESCRIPTION: SEQ ID NO:6:

Ala Met Tyr Ala Pro Pro Ile Ser Gly Gln Ile Arg Cys Ser Ser
1               5                   10                  15

(2) INFORMATION FOR SEQ ID NO:7:

(i) SEQUENCE CHARACTERISTICS:
        (A) LENGTH: 15 amino acids (B) TYPE: amino acid (D) TOPOLOGY: linear (xi) SEQUENCE DESCRIPTION: SEQ ID NO:7:

Ile Arg Cys Ser Ser Asn Ile Thr Gly Leu Leu Leu Thr Arg Asp
1               5                   10                  15

(2) INFORMATION FOR SEQ ID NO:8:

(i) SEQUENCE CHARACTERISTICS:
        (A) LENGTH: 13 amino acids (B) TYPE: amino acid (D) TOPOLOGY: linear -continued (xi) SEQUENCE DESCRIPTION: SEQ ID NO:8:

```
Ala Pro Thr Lys Ala Arg Arg Val Gln Arg Glu Lys Arg
1               5                   10
```

ANTIBODIES SPECIFIC FOR CD4-BINDING DOMAIN OF HIV-1

RELATED APPLICATIONS

This application is a continuation-in-part of application Ser. No. 07/531,789 filed on Jun. 12, 1990 now abandoned, which is a continuation-in-part of Ser. No. 07/342,950, filed on Apr. 25, 1989 abandoned.

FIELD OF THE INVENTION

The invention relates to antibodies which target the CD4-binding region of gp120 HIV-1, and which neutralize HIV-1.

BACKGROUND OF THE INVENTION

Acquired immunodeficiency syndrome (AIDS) is caused by a virus which has at various times been called human T-cell lymphotropic virus type III (HTLV-III), or lymphadenopathy-associated virus (LAV). The virus is currently known as human immunodeficiency virus type 1 (HIV-1).

HIV-1 damages the immune system by infecting and depleting T helper/inducer lymphocytes (hereinafter referred to as "T cells"). T cells are essential because they control the production of antibodies by the B cells, the maturation of cytotoxic T lymphocytes (killer T cells), the maturation and activity of macrophages and natural killer cells, and directly and indirectly, numerous other regulator and effector functions of the immune system.

Infection of a T cell occurs through interaction between an epitope borne by HIV-1 and a receptor site which is located on the T cell surface. This receptor site on the T cell is a protein molecule known as the CD4 antigen. The epitope on HIV-1 is borne by the external envelope glycoprotein gp120 (molecular weight about 120,000 daltons).

The glycoprotein gp120 is produced when a precursor glycoprotein gp 160, made in the HIV-1-infected T cell, is cleaved apart into a transmembrane portion gp41 (molecular weight about 41,000 daltons) and gp120. Glycoprotein gp41 spans through the membrane lipid bilayer of the vizions and of the infected cells and its exterior portion is associated with gp120 through noncovalent binding. Glycoprotein gp120 bears a site which fuses with target cells, whereby the genetic material of the virus enters the cell.

Since the CD4 antigen was identified as the cell-surface receptor for HIV-1, it has been repeatedly shown that soluble forms of CD4 antigen (sCD4) can block the infectivity of the virus. Soluble CD4 inhibits diverse variants of HIV-1, indicating that all these viruses may share a relatively conserved CD4-binding region. Lasky et al. have identified a gp120-specific murine monoclonal antibody (Mab) capable of inhibiting the interaction between gp120 and CD4. *Cell,* 50:995–985 (1987).

The epitope recognized by this Mab has been mapped to a conserved region within amino acid residues 413–456 (numbered according to Human Retroviruses and AIDS, Los Alamos National Laboratories, 1990) where HIV-1 and distantly related HIV-2 share significant homology. This domain of gp120 appears to be important in binding to CD4. However, the CD4-binding region of the envelope glycoprotein gp120 does not appear to be immunogenic in HIV-1 infected persons, since there is very little antigenic cross-reactivity against envelope proteins between sera from patients infected with HIV-1 or HIV-2. Clavel, R. et al., *Science,* 233:343–346 (1986).

SUMMARY OF THE INVENTION

This invention pertains to an epitope located in the region of the envelope glycoprotein gp120 of HIV-1 which binds to the CD4 receptor of T cells, and to antibodies which bind to this epitope. The epitope is located at about amino acid residues 423–437 of gp120. Antibody reactive with the epitope can inhibit T cell infection by diverse strains and isolates of HIV-1.

The antibodies of the invention (and related antibodies) can be used as therapeutic agents, or vaccines, against AIDS, AIDS related complex (ARC), or to treat HIV-infected but asymptomatic individuals. The whole antibody, or a fragment, can be used. Alternatively, such antibody can be conjugated to cytotoxic or antiviral agents, or to a microcarrier (for example, a liposome) which contain such an agent, to produce an immunoconjugate which targets the delivery of the agent to HIV-1 infected cells. The targeted delivery of a therapeutic agent can also be achieved with bispecific antibodies derived from the antibody of this invention. Bispecific antibodies have a second specificity for the agent to be delivered to the target.

The antibodies of this invention include those derived wholly from mice or other animals, as well as wholly human antibodies (which are most preferred for in vivo use), or animal/human chimeric antibodies or humanized antibodies, in which only the antigen-binding regions and some of the framework variable regions are animal derived.

Other uses for the monoclonal antibodies of the invention, such as developing anti-idiotypes for use in diagnostic assays or antibody screening, or using the antibodies in screening for HIV-1 virions or infected cells in standard assay formats, such as an ELISA, are also possible.

Peptides corresponding to the gp120 epitopes of this invention could also be used to stimulate a neutralizing immune response against HIV-1. A preferred peptide has the amino acid sequence IINMWQKVGKAMYAP SEQ ID NO:1 or a functional equivalent thereof.

DETAILED DESCRIPTION OF THE INVENTION

The epitopes of this invention are located on gp120 within the region which binds to the CD4 receptor of T cells. The CD4 receptor binding epitope contains a segment having the amino acid sequence IINMWQKVGKAMYAP. This sequence corresponds to residues 423–437 of gp120 (numbered according to Human Retroviruses and AIDS, los Alamos National Laboratories, 1990). Antibodies against the epitope can inhibit HIV-1 infection with high potency. For example, the monoclonal antibodies which were specific for the epitope all inhibited several HIV-1 isolates. In addition, the epitope is highly conserved among HIV-1 strains and isolates; consequently, antibody specific for one or more of these epitopes can inhibit diverse strains and isolates of HIV-1.

Antibodies to this epitope can be made by somatic cell fusion techniques. See generally, G. Kohler and C. Milstein, *Nature,* 256, 725 (1975); Fung e al., *Biotechnology* 5:940–946 (1987). In brief, an animal such as a mouse is immunized with gp120 of HIV-1. The gp120 can be purified, or partially purified from viral lysates for this purpose. The purification of gp120 can be accomplished by affinity chromatography with antibody against gp120. After immunization, B cells are taken from the immunized animal and then fused with immortalizing cells such as myeloma cells.

Hybridomas which produce antibody that binds to the epitope can be identified by a screening procedure. In such a screening procedure, the hybrid cells are first tested for production of antibody against gp120, preferably with an enzyme-linked immunosorbent assay (ELISA) or a Western blot assay. The assay is run on each of the hybrid cells and hybrid cells which are positive are selected for further analysis. Those that show highest reactivities are ultimately selected. The antibodies can be tested for crossreactivity among different virus isolates by immunofluorescence staining on the surface of virally-infected cells and by radioimmunoprecipitation assays with metabolically radiolabeled viruses. See e.g., Fung et al., supra.

After identification of antibodies reactive with gp120 by the above-described techniques, the antibodies can be tested for neutralizing activity, which is preferably determined by two assays, the first being a virus neutralization assay, described in Ho, D. D. et al., *Science,* 239:1021–1023 (1988). This assay measures the extent of inhibition of HIV-1 infectivity in H9 cells. The second neutralization test is based on the extent of syncytium inhibition as described by Nara, P. L. et al., *AIDS Res. Hum. Retroviruses.* 3:283–302 (1987). HIV-1 and antibody are added to a well seeded with $CD4^+$ CEM-SS cells. CEM-SS cells infected by HIV-1 will express gp120 on the cell surface and form syncytium with the neighboring $CD4^+$ CEM-SS cells. The neutralization of HIV-1 by the Mab is manifested as the inhibition of syncytium formation.

The epitope to which the HIV-1-inhibiting antibodies bind is then identified. This can be accomplished by constructing peptides which correspond to the various regions and which overlap with each other by five amino acids. Reactivity with the peptides can then be examined in a standard immunoassay such as an ELISA. In particular, the antibodies can be examined for reactivity with the I15P region of gp120, having the sequence IINMWQKVGKAMYAP SEQ ID NO:1 (or analogous sequences).

The therapeutic uses for the monoclonal antibodies of the invention include both in vivo immunotherapy and extracorporeal immunotherapy. Direct in vivo treatment with the monoclonal antibodies of this invention involves administering the antibodies internally, preferably via intravenous injection. If treatment of infected cells in the brain is needed, the antibodies can be coupled to an agent, such as certain lipophilic substances, which allows it to pass through the blood-brain barrier. The antibodies of this invention can inhibit T cell infection by different strains and isolates of HIV-1 and thus, they can effectively protect against the different types of virus encountered in the patient population.

With established genetic engineering techniques it is possible to create antibodies which have animal-derived and human-derived portions. Such chimeric antibodies comprise an antigen-binding (variable) region derived from an animal antibody and a constant region derived from a human antibody. The animal can be a mouse or other rodent such as a rat. If the variable region of the chimeric antibody is mouse-derived while the constant region is human-derived, the chimeric antibody will generally be less immunogenic than a "pure" mouse-derived monoclonal antibody, and probably more suited for therapeutic use.

Chimeric antibodies can be produced by chimeric DNA constructs which encode the component antibody chains. See V. T. Oi et al., *Bio Techniques* 4(4):214–221 (1986); L. K. Sun et al., *Hybridoma* 5 (1986). Such a DNA construct comprises DNA encoding functionally rearranged genes for the variable region of a light or heavy chain of an HIV-1-neutralizing antibody linked to DNA encoding the human constant region. Lymphoid cells such as myelomas or hybridomas transfected with the DNA constructs for light and heavy chain can express and assemble the antibody chains. Humanized antibodies, in which only the antigen binding region and some of the framework regions are animal-derived, are also preferred. A detailed example of how to make one type of humanized antibody appears in U.S. application Ser. No. 07/952,852. As evidence that the methods of maining chimeric and humanized antibodies are well known in the art, see, e.g., U.S. Pat. No. 4,816,567, and International Application No. W084/03712, respectively.

Another substantially non-immunogenic therapeutic alternative is to use human monoclonal antibodies. A preferred method for obtaining immortal antibody-producing B cell lines is to transform the B cells from HIV-1-infected individuals by an Epstein Barr virus. The transformed B cell clones can be screened by their specific reactivity with gp120 and the epitope peptides. Another preferred method is to create human monoclonal expression libraries using a bacteriophage lambda expression vector (e.g. ImmunoZap™ by Stratacyte, La Jolla, Calif.), described in Alting-Mees et al., *Strategies in Molecular Biology,* No. 1, Vol. 3, (Jan. 1990). In essence, this approach involves the amplification of immunoglobulin variable region genes from a population of lymphocytes, followed by the creation of a library in *E. coli* in which the variable region genes of the heavy chain alone or in combination with those of light chains are expressed. Antigens (such as the peptide of the invention) are used in screening to identify clones producing binding domains to the antigen. Once the antigen-specific variable region genes are identified, they can be linked to the desirable human constant region genes by a method similar to that used in the production of a chimeric antibody described above.

In a further embodiment of this invention, the monoclonal antibodies can be used to aid in the delivery of cytotoxic or antiviral agents, by forming immunoconjugates comprising the antibody or fragment thereof conjugated to a toxin. Exemplary cytotoxic agents include cytotoxic steroids, gelonin, abrin, ricin and phospholipases. Examples of antiviral agents are interferon, azidothymidine and ribavirin. A particularly preferred toxin used with antibodies of this invention is pokeweed antiviral protein (PAP-S). The immunoconjugates can be formed by chemically linking the antibody and the toxin or by recombinant DNA technology.

Another form of monoclonal antibody is a bispecific hybrid antibody, which carries two different antigen binding portions, both of different specificity. One antigen binding portion can be derived from the monoclonal antibodies of the invention, and a second antigen binding portion can be of a specificity for an agent to be targeted to a particular site. For example, the second specificity can be for a surface epitope of a human T cell or a macrophage, such as the CD4 molecule. These bispecific antibodies can be used to target a T cell or macrophage toward an HIV-1 infected cell.

The bispecific antibodies can be single, hybrid antibodies or antibody fragments having a bispecificity (See M. Brennan, "A Chemical Technique for the Preparation of Bispecific Antibodies from Fab' Fragments of Mouse Monoclonal $IgG_1$", *Biotechniques* 4:424–27 (1986)) or they can be heteroaggregates of two antibodies each having a different specificity.

The antibodies of this invention are particularly suitable for passive immunization because they can cross-protect against HIV-1 of different strains in the population. In this procedure, patients who are asymptomatic (not yet showing symptoms of AIDS or ARC), or who are seronegative but in a high risk group, are treated to prevent infection. The targets include fetuses carried by or babies born to HIV-1-carrier mothers, and health professionals working with AIDS patients or with infected blood products. The agent for treatment, again, can be the monoclonal antibodies of the invention, chimeric monoclonal antibodies, or bispecific monoclonal antibodies.

The monoclonal antibodies of the invention can also be used to develop anti-idiotype antibodies, with well-known techniques, for use in a diagnostic assay, to determine whether an asymptomatic individual infected with HIV-1 or a patient with AIDS or ARC produces the antibodies reactive with the particular peptide segment of gp120 of HIV-1 strains that are antigenically related in this peptide segment. Such a diagnostic assay could be of several well-known types, including of sandwich or tandem assay type.

The anti-idiotype antibodies could also be used in a drug screening assay to isolate Mabs, or other drugs reactive with the CD4-binding region, and thus potentially useful in therapy.

The preferred neutralizing antibodies of this invention recognize epitopes located in a CD4-binding region of gp120 having the following amino acid sequence:

IINMWQKVGKAMYAP.                           SEQ ID NO:1

This peptide represents amino acid residue numbers 423 through 437 of gp120. An eleven amino acid peptide encompassed by amino acid residue #422–432 and previously identified as the epitope of monoclonal antibody 5C2E5 by Lasky et al., *Cell*, 50:975–985 (1987), did not react with the monoclonal antibodies of this invention.

The peptide immunogens of this invention can include the above-identified amino acid sequences or any functionally equivalent immunochemical and/or immunogenic sequences thereof. These equivalents include, for example, any of the actual epitope portions of any of these sequences, corresponding peptide regions from various HIV-1 strains and peptides generated by various changes such as insertions, deletions and substitutions of amino acids.

The peptides of this invention can be coupled together to form larger, multivalent oligopeptides. The peptides may be prepared by chemical synthesis. Alternatively, they may be prepared by recombinant DNA technology where DNA sequences encoding the peptides are synthesized or isolated from HIV-1 DNA and expressed in an appropriate expression system.

The peptides may also be used individually or in combination to elicit an immune response against HIV-1. For this purpose, the peptides may be formulated in vaccine compositions, generally for administration at concentrations in the range of 1 $\mu$g to 20 mg/kg of host. Physiologically acceptable vehicles such as water, saline, or phosphate buffered saline (PBS) can be used in the formulations. Adjuvants, such as aluminum hydroxide gel, can also be employed. The route of administration can be intramuscular, intraperitoneal, subcutaneous, or intravenous. The compositions can be given as many times and as often as needed, usually at one to four week intervals.

In preferred embodiments of the vaccine composition, the peptides are coupled to a carrier protein such as a foreign keyhole limpet hemocyanin. This can enhance the immunogenicity of the haptenic peptides. The peptides may be used in immunoassays to identify neutralizing antibody or to screen for the presence of neutralizing antibody in serum.

This invention is illustrated further by the following examples.

EXAMPLE 1

Production and Testing of Monoclonal Antibodies Reactive Against the CD4-Binding Domain of gp120

A. Materials and Methods

1. Antibody Production and Screening

The envelope glycoprotein, gp120, of HTLV-IIIB was prepared from H9/HTLV-IIIB cell extracts. H9/HTLV-IIIB cells were lysed with a lysing buffer consisting of 10 mM Tris-HCl, pH 7.5, 120 mM NaCl, 1 mM $MnCl_2$, 0.5% Triton X-100 and 0.1 mM phenylmethyl sulfonyl fluoride. The extracts were heat-inactivated for 1 hour at 56° C. and reacted with lentil-Sepharose (Sigma, St. Louis, Mo.). The bound fraction was eluted and incubated with Affigel-10 coupled with a murine monoclonal antibody against gp120 (BAT123). See Fung et al. *Biotechnology*, 5:940–946 (1987). The viral gp120 fraction was eluted and used as the immunogen. Five male BALB/c mice were immunized with 25 $\mu$g of protein in Freund's complete adjuvant and three subsequent immunizations of 25 $\mu$g in the same adjuvant at 1-month intervals. Three days after the final booster immunization, the mice were sacrificed and spleen cells were isolated and fused with SP2/0 myeloma cells as described by Fung et al., (supra). Hybrids were selected by supplementing the growth medium with 0.1 mM hypoxanthine, 0.4 $\mu$M aminopterin and 16 $\mu$M thymidine. Two weeks later, supernatants were collected from the wells of the microtiter plates. Each well had about 10 hybrid colonies after 10 days. There were estimated to be about 140,000 hybridomas for consecutive screening by ELISA with the peptide T35S and gp120 as coating antigens. Peptide T35S is a synthetic peptide containing the CD4-binding region as delineated by Lasky et al., (supra). Mab from hybridomas selected for further characterization were produced in mouse ascites and purified by protein A affinity chromatography. A total of 7 outgrowths giving the strongest positive reactions in both screening assays were single-cell cloned by limiting dilution, and the supernatants were screened by ELISA using T35S as the coating antigen. These seven Mabs are designated as the G3 series, respectively identified as G3-42, G3-211, G3-299, G3-508, G3-519, G3-536, and G3-537. The hybridoma cell lines producing the antibodies G3-519, G3-508, and G45-60 were deposited with the American Type Culture Collection, 10801 University Blvd, Mannassas, Va., 20110 on May 15, 1991, and respectively assigned Depository Identification numbers HB 10747, HB 10748, and HB 10749. They are all IgG1 subclass.

The same immunization described above was then performed on two other mice. After their sacrifice, the same fusion procedure described above was performed. Selection of hybrids was also as described above, but 60 96-well plates were used, there being about 10 clones per well, yielding about 60,000 colonies of hybridomas. Consecutive screening by ELISA with the peptide gp120 indicated 635 positive wells (represented by an optical density (O.D.) on ELISA of >0.25). These hybridomas were selected and grown as described above, and those four with the strongest positive reactions in the screening assay were single-cell cloned by limiting dilution, the supernatants being screened by ELISA with gp120 as the coating agent. The four Mabs, all IgG1 subclass are designated the G45 series, respectively identified as G45-60, G45-16, G45-70, and G45-89.

2. Characterization of Mabs for Reactivities with Diverse HIV-1 Isolates G3 series Mabs Were Tested for Reactivity With Other HIV-1 Isolates.

H9 cells persistently infected with HTLV-IIIB, HTLV-IIIRF, HTLV-IIIMN, HTLV-IIIAL, HTLV-IIIWMJ, HTLV- IIIZ34, and HTLV-IIIZ84 were maintained in RPMI-1640 medium supplemented with 10% heat-inactivated fetal bovine serum, 100 U/ml penicillin and 100 μg/ml streptomycin. Cell-free culture supernatants from H9 cells infected with HTLV-IIIB, HTLV-IIIRF, and HTLV-IIIAL containing high levels of reverse transcriptase activity were frozen in aliquots and used for neutralization assays as described below.

3. Immunofluorescence Staining

The method for immunofluorescence staining of HIV-1 infected H9 cells was described by Fung et al. (supra). Fifty μl aliquots of H9 cells at 5×10⁶ cells/ml was added to 1.5 ml microfuge tubes. Fifty μl of protein A-purified Mab (5 μg/ml) was added and incubated for 30 minutes at 4° C. The tubes were then centrifuged at 300 ×g for 5 minutes, the supernatant removed, and the cells washed with RPMI-1640 containing 2% fetal bovine serum and 0.1% sodium azide. The tubes were tapped to loosen the cells. Ten μl of fluorescein isothiocyanate (FITC)-conjugated goat anti-mouse IgG (Tago, Burlingame, Calif.) was added at a dilution of 1:200 in phosphate buffered saline (PBS) and incubated for 30 minutes at 4° C. After the cells were washed, they were suspended in PBS, placed on slides, mounted and examined with a fluorescence microscope. The controls were uninfected H9 cells and antibodies of irrelevant specificities.

For the G45 series Mabs, the same staining procedures were used to test binding to certain HIV-1 isolates. But, the cells were fixed with 0.5% paraformaldehyde and then analyzed by flow cytometric methods (Kim et al., 1990. *J. Immunol.* 144:1257).

4. Enzyme-linked Immunosorbent Assay (ELISA)

The screening and epitope mapping of Mabs were performed by ELISA. The reactivities of HIV-1 seropositive patient sera to the peptide T35S were also tested by ELISA. Sera was collected randomly from 65 HIV-1 seropositive patients. Thirty of these subjects had AIDS, 19 had AIDS-related complex, and 16 were asymptomatic. Sera from 10 HIV-1 seronegative donors were also tested as control.

In the ELISA, wells of Immulon 2 microtiter plates (Dynatech, Chantily, Va.) were coated overnight at r.t. with 100 μl of synthetic peptides (5 μg/ml, but 0.5 μg/ml for T35S) or 100 μl of purified gp120 (0.1 μg/ml) in PBS. They were then incubated with 5% BLOTTO in PBS for 1 hour at r.t. and washed with PBS-Tween 20 (0.05%). Next, 100 μl culture medium, or 100 μl purified mouse Mab (diluted with PBS/Tween 20 to 0.4 μg/ml) or 100 μl diluted human serum (diluted with BLOTTO buffer 1:100) was added and the wells were incubated for 1 hour at r.t. with the appropriate goat anti-mouse IgG or goat anti-human IgG conjugated with horseradish peroxidase (diluted with 5% BLOTTO in PBS). After another washing step, bound antibodies were visualized by reaction with 0.1% tetramethylbenzidine and 0.0003% hydrogen peroxide as substrates. The optical density (OD) of the reaction solution was read at 450 nm.

5. Generation of gp120 Peptides

Peptide T35S was synthesized and characterized by Peninsula Laboratories (Belmont, Calif.). All other peptides used in this study were synthesized using the RaMPS peptide synthesis system of DuPont (Wilmington, Del.), employing a FMOC (9-fluorenylmethoxycarbonyl) synthesis protocol described in the manual. The purity of the RaMPS-synthesized peptides was characterized by high performance liquid chromatography and the predicted structure was assessed by fast atom bombardment/mass spectrometry analysis. Amino acid residues and the sequences of the synthetic peptides were derived from the HXB2 clone of HIV-1, Myers, G. et al., *Human Retroviruses and AIDS*, Los Alamos Natl LAb., Los Alamos, N.Mex. (1988), as shown in Table 1.

TABLE 1

Locations and sequences of synthetic peptides within the CD4-binding region of gp120 of HTLV-IIIB[a]

| Peptide | Amino acid residue number | Sequence | |
|---|---|---|---|
| T35S | (413–447) | TITLPCRIKQIINMW-QKVGKAMYAPPISGQIRCSSA | SEQ ID NO: 2 |
| T15W | (413–427) | TITLPCRIKQIINMW | SEQ ID NO: 3 |
| QIIK | (422–432) | QIINMWQKVGK | SEQ ID NO: 4 |
| I15P | (423–437) | IINMWQKVGKAMYAP | SEQ ID NO: 5 |
| A15S | (433–447) | AMYAPPISGQIRCSS | SEQ ID NO: 6 |
| I15D | (443–457) | IRCSSNITGLLLTRD | SEQ ID NO: 7 |

[a]The amino acid residues and sequences were adopted from Myers et al., (supra).

6. Radioimmunoprecipitation Assay (RIPA)

The reactivity of the G3 series antibodies was tested by an established RIPA protocol. Ho, D. D. et al., *Science* 239:1021–1023 (1988). Briefly, H9 cells (infected with HTLV-IIIB, HTLV-IIIRF, HTLV-IIIAL, and HTLV-IIIWMJ) were metabolically labelled for 4 hours with [³⁵S] cysteine and [³⁵S] methionine (100 μCi/ml) (ICN, Irvine, Calif.) and suspended in a RIPA lysing buffer (50 mM Tris-HCl, pH 8.0, 150 mM NaCl, 1% Triton X-100, 1% Na deoxycholate, 0.1% SDS, and 1 mM phenylmethyl sulfonyl fluoride). Lysates were precleared with protein A-Sepharose bound with rabbit antiserum to mouse k light chain (k-PAS) for 3 hours at r.t. RIPA was performed by adding 3 μg purified mouse Mab, 0.3 ml of 10% suspension of k-PAS to 200 μl of labelled and clarified lysate. The samples were incubated for 18 hours at 4° C. and the beads were washed with the RIPA lysing buffer. The pellets were suspended in electrophoresis sample buffer and boiled for 3 minutes. Proteins were analyzed by SDS-polyacrylamide gel electrophoresis followed by autoradiography.

7. Neutralization Assays of HIV-1

Virus neutralization studies on the G3 series Mabs were performed using two different assays: a syncytium-forming assay using CEM-SS cells as described by Nara et al., *AIDS Res. Human Retroviruses*, 3:283–302 (1987), and a second neutralization assay using H9 cells as described by Ho et al., (supra). Only the syncytium forming assay was used for G45 series.

For the syncytium forming assay, two-fold serial dilutions of Mabs were made in RPMI-1640 medium supplemented with 10% heat inactivated fetal bovine serum. Fifty microliters of each diluted antibody were mixed with an equal volume of virus (100 syncytium-forming units or SFUs) and incubated for 1 hour at r.t. The mixtures were added to two poly-L-Lysine-treated microtiter wells containing 5×10⁴ DEAE-dextran treated CEM-SS cells and incubated for 3–4 days. The number of syncytia formed were counted using an inverted microscope. The neutralization titers were determined by using the 50% (Vn/Vo=0.5) neutralization point. Vn represents the number of virus-induced SFUs in the test wells and Vo represents the total number of virus induced SFUs in the control when growth medium alone was added.

The second neutralization assay measured the extent of the inhibition of HIV-1 infectivity in H9 cells. In this assay, 100 μl of virus inoculum (50 TCID$_{50}$) was preincubated with 100 μl of test antibodies of different concentrations for 1 hour at 37° C. before inoculation into 0.75×10$^6$ H9 cells in 1.5 ml of RPMI-1640 medium supplemented with 15% fetal bovine serum, 10 mM HEPES (N-2-hydroxyethyl piperazine-N'-2-ethane sulfonic acid), 250 U/ml penicillin, 250 μg/ml streptomycin, and 2 mM L-glutamine. On day 7, cell-free culture supernatants were collected for assay of HIV-specific p24 antigen by ELISA (Abbott Laboratories, N. Chicago, Ill.).

Another neutralization assay using G3-519 to several patient HIV-1 isolates was performed by another method, as described in Ho, D. D. et al., N. Engl. J. Med. 1989, 321:1621. 50 TCID$_{50}$ of patient HIV-1 isolates were used to infect 1×10$^6$ PHA-stimulated peripheral blood mononuclear cells (PBMC) from HIV-1 seronegative clones. Varying concentrations of Mabs were incubated with the virus for 1 hr at 37° C. before infection. On day 7–10, culture supernatants were collected for p24 assays (described below) to monitor HIV-1 infection.

8. HIV-1-binding Inhibition Assay

For the G3 series, a binding inhibition assay as described by Ho, D. D. et al., (supra), was used. Briefly, a concentrated preparation of HIV-1 virions (10 μl) was pretreated with 10 μl of the Mab (1 mg/ml) for 30 minutes at r.t. before incubation with C8166 cells (5×10$^5$, 30 minutes at 37° C.). Subsequently, the cells were washed and suspended in 25 μl of human anti-HIV-1 conjugated to FITC (diluted 1:50). After 30 minutes at 4° C., the cells were then washed, fixed in 1% paraformaldehyde, and analyzed by flow cytometry.

B. Results

1. Generation and Characterization of gp120 Specific Mab

The seven G3 series Mabs and the G45 series, isolated by the methods detailed herein are reactive with other HIV-1 strains, such as HTLV-IIIRF, -MN, -AL, -Z84 and -Z34. This was confirmed by indirect immunofluorescence staining of the surface of virus-infected cells (Table 2).

TABLE 2

Immunofluorescence staining of anti-CD4-binding-region antibodies with H9 cells bifected with 6 different strains of HIV-1[a]

| Mab | HTLV-III | | | | | |
|---|---|---|---|---|---|---|
|  | B | RF | MN | AL | Z84 | Z34 |
| G3-42 | + | ++ | ++ | ++ | +++ | + |
| G3-211 | + | ++ | ++ | ++ | +++ | + |
| G3-299 | + | + | ++ | + | ++ | + |
| G3-508 | + | ++ | ++ | ++ | +++ | + |
| G3-519 | + | ++ | ++ | ++ | +++ | + |
| G3-536 | + | + | ++ | ++ | +++ | + |
| G3-537 | + | + | ++ | ++ | +++ | + |
| G45-60[b] | + | ++ | ++ | n.t. | n.t. | n.t. |

[a]The relative intensity of immunofluorescence is indicated by the number of "+" signs.
[b]The other members of the G45 series were not tested for binding.

Using metabolically labeled HTLV-IIIB, HTLV-IIIRF, HTLV-IIIAL and HTLV-IIIWMJ infected H9 cell lysates, the G3 series Mabs were also examined by radioimmunoprecipitation assays. All 7 G3 series Mabs specifically precipitated both gp120 and gp160 of diverse HIV-1 isolates as summarized in Table 3. This further indicates the broad reactivity of these antibodies to many strains of HIV-1.

| | HTLVIII | | | |
|---|---|---|---|---|
| Mab | B | RF | AL | WMJ |
| G3-42 | ++ | + | + | + |
| G3-211 | ++ | + | + | + |
| G3-299 | ++ | + | + | + |
| G3-508 | ++ | + | + | + |
| G3-519 | ++ | + | ++ | + |
| G3-536 | +++ | + | + | + |
| G3-537 | +++ | + | ++ | + |

[a]The relative intensity of the gp120 protein band on the autoradiographs is represented by the number of "+" signs.

2. Neutralization of HTLV-IIIB, HTLV-IIIRF, HTLV-IIIAL, and HTLV-IIIZ84 Infectivity In the syncytium-forming assay, syncytia were counted on day 3 or 4. To determine whether a group-specific neutralizing immune response was a feature of the Mabs to the CD4-binding region, HTLV-IIIB and HTLV-IIIRF isolates were used, which differ by 21.4% in their predicted amino acid sequence in gp120, as well as HTLV-IIIZ84 (from Zaire) and HTLV-IIIAL (from Haiti), which are known to differ from the former strains. The seven G3 series Mab showed varying neutralizing activities against the isolates HTLV-IIIB and HTLV-IIIRF. The ID$_{50}$ (50% inhibitory dose, i.e. the Mab concentration at which the infection of target cells by HIV-1 is inhibited by 50%) for each G3 series Mab against both HTLV-IIIB and HTLV-IIIRF is listed in Table 4. Table 4 also shows syncytium formation inhibition of G3-519 and G45-60 against HTLV-IIIMN and HTLV-IIIZ84.

The data in Table 4 suggest that (as measured by both syncytium inhibition and the H9 cell infectivity assay), G3-299 is strongest in neutralization of HTLV-IIIB, whereas G3-519 is the most potent in neutralization of HTLV-IIIRF. The majority of these Mabs require high doses (>10 μg/ml) to achieve 50% neutralization of the input HIV-1.

As measured by syncytium inhibition alone, G45-60 was substantially equal to G3-519 in neutralizing HTLV-IIIRF and HTLV-IIIMN. But G45-60 was substantially more effective in neutralizing HTLV-IIIZ84.

Similar results of HIV-1 neutralization were obtained for the G3 series Mabs using the H9 cell infectivity assay. These results are summarized in Table 4. Again, the most potent antibodies were G3-299 and G3-519 in the neutralition of HTLV-IIIB and HTLV-IIIRF, respectively. HTLV-IIIAL was particularly sensitive to neutralition by G3-508, G3-519, G3-42 and G3-536. The ID$_{50}$ for G3-508 and G3-519 were both less than 0.2 μg/ml (Table 4). Several Mabs required greater than 10 μg/ml to neutralize HIV-1 infectivity by 50%.

| | Syncytium-Forming Assay using CEM cells (ID$_{50}$ in μg/ml) | | | |
|---|---|---|---|---|
| Mab | HTLV-IIIB | HTLV-IIIRF | HTLV-IIIMN | HTLV-IIIZ84 |
| G3-42 | 3.4 | >50.0 | n.t. | n.t |
| G3-211 | 13.4 | 18.8 | n.t. | n.t. |
| G3-299 | 2.1 | 11.1 | n.t. | n.t. |
| G3-508 | 8.0 | 10.4 | n.t. | n.t. |
| G3-519 | 5.7 | 1.8 | 0.37 | >>20 |
| G3-536 | 21.4 | 42.1 | n.t. | n.t. |

-continued

Syncytium-Forming
Assay using CEM cells ($ID_{50}$ in µg/ml)

| Mab | HTLV-IIIB | HTLV-IIIRF | HTLV-IIIMN | HTLV-IIIZ84 |
|---|---|---|---|---|
| G3-537 | 12.5 | 38.6 | n.t. | n.t. |
| G45-60 | 5.0 | 1.9 | 0.22 | 5.1 |

Infectivity Assay Using H9 Cells
($ID_{50}$ in µg/ml)

| Mab | HTLV-IIIB | HTLV-IIIRF | HTLV-IIIAL |
|---|---|---|---|
| G3-42 | 1.2 | 25.0 | 0.2 |
| G3-211 | 10.0 | 22.0 | 12.0 |
| G3-299 | 0.5 | 10.0 | 20.0 |
| G3-508 | 6.0 | 0.6 | <0.2 |
| G3-519 | 20.0 | 0.3 | <0.2 |

-continued

Infectivity Assay Using H9 Cells
($ID_{50}$ in µg/ml)

| Mab | HTLV-IIIB | HTLV-IIIRF | HTLV-IIIAL |
|---|---|---|---|
| G3-536 | 30.0 | 5.0 | 0.3 |
| G3-537 | 30.0 | 15.0 | 12.0 |

3. Preparation and Neutralization of Patient HIV-1 Isolates by G3-519

A neutralization study using G3-519 was conducted against some HIV-1 primary isolates obtained from the plasmas of eight AIDS patients from the Los Angeles area. These primary HIV-1 isolates were used to infect PHA-stimulated seronegative peripheral blood mononuclear cells ("PBMC"). On day 7 to day 10 the culture supernatants containing the patient viral isolates were collected by centrifugation of the cell cultures. The culture supernatant was assayed for p24 concentration, using the p24 ELISA made by Abbott Laboratories, Inc.

G3-519 showed neutralizing activity ($ID_{50}$<5 µg/ml) for four of the eight patients, limited neutralizing activity for one patient ($ID_{50} \geq 5$ µg/ml), and no neutralizing activity in three patients.

4. Delineation of the Epitope in the CD4-binding Region

To map the epitope location more precisely in the CD4-binding region on gp120, 4 peptides (T15W, I15P, A15S, and I15D) each respectively overlapping the next by 5 amino acids, and the fifth peptide Q11K identified as the epitope of Mab 5C2E5 (Lasky, L. A., et al., supra.) were synthesized (Table 1). ELISA against this group of peptides was performed using the seven Mabs. All of the Mabs bind to I15P very strongly (OD>1.0), but not to its adjacent peptides (OD<0.1) (Table 5). It is interesting to note that the peptide Q11K, (Lasky, L. A. et al. (supra) an eleven amino acid peptide encompassed almost entirely by peptide I15P except the N-terminal glutamine, does not exhibit appreciable reactivity to any of the seven Mabs under these experimental conditions.

TABLE 5

Reactivity of mabs to HIV-1 envelope gene-encoded synthetic peptides in ELISA[a].

| Peptide | G3-42 | G3-211 | G3-299 | G3-508 | G3-519 | G3-536 | G3-537 |
|---|---|---|---|---|---|---|---|
| T35S | + | + | + | ++ | + | + | + |
| T15W | − | − | − | − | − | − | − |
| Q11K | − | − | − | − | − | − | − |
| I15P | + | + | + | ++ | + | + | + |
| A15S | − | − | − | − | − | − | − |
| I15D | − | − | − | − | − | − | − |

| Peptide | G45-60 | G45-16 | G45-70 | G45-89 |
|---|---|---|---|---|
| T35S | + | + | + | + |
| T15W | − | − | − | − |
| Q11K | − | − | − | − |
| I15P | + | + | + | + |
| A15S | − | − | − | − |
| I15D | − | − | − | − |

[a]The procedure of ELISA is described in Materials and Methods. The reading of these Mabs to various coated synthetic peptides is regarded as negative (−) when the OD is less than 0.1; positive (+) when the OD is greater than 1.0

5. Inhibition of HIV-1 binding to $CD4^+$ Cells

All seven G3 series Mabs (i.e., G3-519; G3-508; G3-42; G3-211; G3-299; G3-536; G3-537) directed against amino acids 423–437 of gp120 exhibited significant inhibition of binding of HTLV-IIIB or HTLV-IIIRF to $CD4^+$ C8166 cells. Despite the substantial differences in their capacity to neutralize HIV-1, the inhibitory activities of these Mabs on the specific binding of HIV-1 to the $CD4^+$ C8166 cells were comparable. In contrast, BAT123, a mouse Mab specific, for the central hypervariable loop of gp120 (amino acid residues 300–330; Fung et al., supra.) had no effect on HIV-1 binding to the target cells.

6. Reactivity with Mutant Forms of gp120

A panel of gp120 mutants was used to determine whether the binding of the G3 antibodies was influenced by alterations in the gp120 amino acid sequence outside of the core binding epitope. Culture supernatant (100 µl) from COS-1 cells transfected 48 hours previously with 10 µg of pSVII-Ienv plasmid expressing either wild type or mutant HIV-1 (HxBc2) envelope glycoproteins were supplemented with 20 mM Hepes buffer (pH 7.0). The gp120 molecules in the supernatants were captured onto the microtest plate precoated with sheep anti-gp120 C-terminal peptide (D6205). The peptide sequence of the peptide is Ala Pro Thr Lys Ala Arg Arg Val Gln Arg Glu Lys Arg (SEQ ID NO:8) representing amino acid residue numbers 497–511 of gp120. After washing away unbound gp120, MAbs were added (usually at 1 µg/ml; 6.7 nM) in TMSS buffer plus 0.5% Tween-20. Bound MAbs were detected.

The G3 antibodies were tested against 63 gp120 mutants, and a determination was made as to which amino acid changes seriously impaired binding (a reduction of 3-fold or more). In addition to changes in the C4 core epitope, a change in the V3 loop region inhibited binding. Specifically, the binding of the antibodies G3-508, G3-519, and G45-60 was inhibited by switching Gly to Trp at position 314 of gp120. Other changes in gp120 inhibiting binding were an Ala to Leu switch at position 433 and a Tyr to His switch at position 435. It is also noted that an Asn to Thr switch at position 262 enhanced binding by these three antibodies.

7. Reactivity of Serum from HIV-1 Infected Individuals with the CD4-binding Region Peptide T35S Serum samples from patients with AIDS (N=30) or ARC (N=16), asymptomatic HIV-1 seropositive individuals, and normal healthy donors (N=10) were analyzed for reactivity with the peptide T35S by ELISA. For each serum sample, an OD value was calculated as the difference between the average absorbance of two peptide-coated wells and two PBS-treated wells. The cut-off OD (0.075) represented the mean OD+2SD for 10 seronegative serum samples. The results of the ELISA indicate that the immunoreactivity exhibited by sera from patients with AIDS or ARC are not significantly different from those of normal control samples. Among the 30 AIDS and 19 ARC patients studied, no detectable antibodies to the peptide T35S were found. Only serum samples from two of the 16 asymptomatic seropositive individuals giver signals significantly above the cut-off point.

EXAMPLE 2

Immunoconjugates of PAP-S and Mabs

Immunoconjugates can be pared by chemically coupling different murine neutralizing monoclonal antibodies which recognize the CD4-binding domain of gp120 of HIV-1 to PAP-S through a disulfide bond linkage. These immunoconjugates, as exemplified by G3-519-PAP-S, can show specific cytotoxicity against human T cells infected with various strains and isolates of HIV-1. The epitope mapping studies described above, using synthetic polypeptides, have revealed that Mab G3-519 recognized a relatively conserved region (amino acids number 423–433) of gp120.

This example illustrates the preparation and efficacy of an immunoconjugate comprising pokeweed antiviral protein (PAP-S) and Mabs reactive against an epitope on the CD4-binding region of gp120.

A. Materials and Methods

1. Purification of PAP-S

PAP-S was purified from seeds of *Phytoacca americana* (pokeweed) using a method of Barbieri et al. (Barbieri, L. et al., (1982) *Biochem.* J. 203:55–59). Briefly, pokeweed seeds (100 g) were homogenized in 500 ml of 5 mM phosphate buffer (pt H 6.0). Insoluble materials and lipid were removed after centrifugation at 10,000×g for 1 hour. Superatant was supplied to a CM-Sepharose Fast Flow (Pharmacia, Piscataway, N.J.) column equilibrated with 5 mM phosphate buffer. After washing, bound proteins were eluted with a NaCl gradient (0–0.3M). The peak containing activity of ribosome inactivation was pooled and dialyzed against PBS using a membrane with molecular weight cut-off of 10,000 daltons.

2. Antibody and Toxin Conjugation

G3-519 Mab (10 mg) were reacted with a heterobifunctional cross-linking reagent, N-succinimidyl-3-(2-pyridyldithio) propionate (Pharmacia) at 1:3 molar ratio as described by Carlsson et al., (Carlsson, J. et al., (1978), *Biochem.* J. 173:723–737). Pokeweed antiviral protein (6 mg) was reacted with 2-iminothiolane at 1:3 molar ratio as described by Lambert, R. et al., (1978), in *Biochemistry* 17:406:416. Excess of chemicals were removed by gel filtration using a 10PD column (Bio-Rad, Richmond, Calif.). Chemically modified antibody and PAP-S were combined and incubated at r.t. for 2 hours or at 4° C. overnight. Uncoupled PAP-S was removed by gel filtration on a Sephacryl S-200 (HR) column equilibrated with PBS. The peaks containing antibody and conjugate were pooled, concentrated to 10 ml and then dialyzed against 5 mM phosphate buffer, pH 6.0. Dialyzed samples were applied to a Mono S (Pharmacia) column and the immunoconjugate was eluted from the column using a NaCl gradient. The composition of the immunoconjugate was analyzed by a 7.5% sodium dodecyl sulfate polyacrylamide gel electrophoresis (SDS-PAGE) under a non-reducing condition (Fast System, Pharmacia) along with molecular weight markers (Bio-Rad).

3. Cytotoxicity Assay of Immunoconjugates

The ability of the G3-519 immunoconjugate to kill HIV-infected cells was assayed by the inhibition of [$^3$H]-thymidine incorporation of infected cells. H9 cells either uninfected or chronically infected by HIV-1 strains (HTLV-IIIB, HTLV-IIIRF, and HTLV-IIIMN) were maintained in log phase in RPMI1640 supplemented with 15% heat-inactivated fetal bovine serum, 100 U/ml of penicillin and 100 µg/ml of streptomycin. One hundred and eighty µl of $5 \times 10^4$ cells/ml were dispensed into each well of a 96-well microtiter plate. Twenty µl of purified immunoconjugate of 5-fold serial dilutions (100 µg/ml–160 ng/ml) were added into the wells in triplicates. The controls were an irrelevant immunoconjugate of PAP-S or a mixture of the unconjugated antibody and PAP-S at equivalent concentrations under the identical conditions. The cell cultures were kept at 37° C. for 24 hours and pulsed with 1 µCi per well of ($^3$H)-thymidine for another 4 hours. Cells were harvested on glass fiber filters using a Skatron cell harvester and the ($^3$H)-thymidine retained on the dry filter was measured by scintillation counting. The inhibition of cellular thymidine incorporation was calculated by comparing the radioactivity of test cultures to that of the control.

To examine the specific cell killing by the immunoconjugate, experiments were performed using unconjugated Mab to compete with the conjugate. 0.6 µg/ml of G3-519-PAP-S, which inhibited 55% of thymidine incorporation was chosen in the study. The infected H9 cells were incubated with the unconjugated Mabs at 37° C. for 30 minutes prior to addition of G3-519-PAP-S.

B. Results

1. Purification and Characterization of the G3-519 Immunoconjugate

The G3-519 immunoconjugate was eluted from the Mono S column as a single peak at 110 mM NaCl concentration. However, this peak, as analyzed by 7.5% SDS-PAGE under the non-reducing condition, resolved into two protein bands, a higher molecular weight band representing the conjugate containing two molecules of PAP-S per molecule of antibody and a lower molecular-weight band representing a conjugate with one molecule of PAP-S per antibody molecule. Densitometric analysis of Coomassie blue stained gels indicated that the higher molecular-weight conjugate accounted for about 25% of the total immunoconjugates.

The binding activity of the immunoconjugate determined by ELISA using synthetic oligopeptides including the binding epitope of G3-519 revealed no impairment of antibody binding activity after conjugation.

2. Cytotoxicity of G3-519-PAP-S to HIV-1 Infected Cells

H9 cells infected separately with three diverse stains of HIV-1 (HTLV-IIIMN, HTLV-IIIRF, HTLV-IIIB) were all sensitive to G3-519-PAP-S treatment. The immunoconjugate killed H9 cells infected with HTLV-IIIMN more effectively ($IC_{50}$=$1.4\times10^{-10}$ M) than those H9 cells infected with HTLV-IIIB ($IC_{50}$=$1.7\times10^{-9}$M). G3-519-PAP-S was not cytotoxic to uninfected H9 cells up to a concentration of $5.3\times10^{-8}$M.

3. Specific Cytotoxicity of Immunoconjugates

The specificity of the G3-519 immunoconjugate against target cells was studied by antibody blocking experiments. Addition of unconjugated G3-519 prior to the incubation of target cells with the immunoconjugates, competed for cell binding with the immunoconjugates and efficiently blocked the cytotoxicity of immunoconjugates in a dose-dependent fashion.

G3-519-PAP-S at 0.6 $\mu$g/ml inhibited 55% of thymidine incorporation of H9 cells infected with HTLV-IIIB. In the presence of 50 fold excess of Mab G3-519, the immunoconjugate inhibited 13% of thymidine incorporation. An irrelevant Mab to hCG, did not inhibit the cytotoxicity of immunoconjugates even at 200 fold excess of this antibody.

These results show that G3-519-PAP-S specifically killed H9 cells infected with three diverse strains of HIV-1, and is thus effective against different strains. Other antibody conjugates against the CD4 region should also be effective in killing cells infected with diverse HIV-1 isolates and strains.

EQUIVALENTS

Those skilled in the art will recognize, or be able to ascertain using no more than routine experimentation, many equivalents to the specific embodiments and examples of the invention described herein. These and all other equivalents are encompassed by the following claims.

What is claimed is:

1. A chimeric monoclonal antibody having variable region of rodent origin and a constant region of human origin which binds to a peptide represented by the amino acid sequence SEQ ID NO:1 in the CD4-binding region of the gp120 of HIV-1 and inhibits in vitro infection of T cells by HTLV-III$_B$.

2. A continuous, stable antibody-producing cell line which produces an antibody of claim 1.

3. A chimeric monoclonal antibody having a variable region selected from the group consisting of the variable regions of G3-519 and G3-508 and a constant region of human origin.

4. A continuous, stable antibody-producing cell line which produces an antibody of claim 3.

* * * * *